United States Patent
Shiba et al.

(10) Patent No.: US 7,329,514 B2
(45) Date of Patent: Feb. 12, 2008

(54) PROCESS FOR PRODUCING N-ACETYLNEURAMINIC ACID

(75) Inventors: Mari Shiba, Saitama (JP); Satoshi Koizumi, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 344 days.

(21) Appl. No.: 10/504,511

(22) PCT Filed: Feb. 28, 2003

(86) PCT No.: PCT/JP03/02332

§ 371 (c)(1),
(2), (4) Date: Aug. 13, 2004

(87) PCT Pub. No.: WO03/072783

PCT Pub. Date: Sep. 4, 2003

(65) Prior Publication Data

US 2005/0142643 A1  Jun. 30, 2005

(30) Foreign Application Priority Data

Feb. 28, 2002 (JP) ............................. 2002-053696

(51) Int. Cl.
C12P 19/26 (2006.01)
C12P 19/28 (2006.01)
C12N 1/20 (2006.01)
C07H 21/04 (2006.01)

(52) U.S. Cl. ..................... 435/84; 435/85; 435/252.33; 536/23.2

(58) Field of Classification Search .................. 435/84, 435/85, 252.33; 536/23.2, 33
See application file for complete search history.

(56) References Cited

U.S. PATENT DOCUMENTS

| | | | |
|---|---|---|---|
| 4,670,389 A | 6/1987 | Uwajima et al. | 435/253 |
| 5,071,750 A | 12/1991 | Kragl et al. | 435/94 |
| 5,795,764 A | 8/1998 | Christgau et al. | 435/200 |
| 5,827,698 A | 10/1998 | Kikuchi et al. | 435/115 |
| 5,908,768 A | 6/1999 | Ono et al. | 435/110 |
| 6,156,544 A | 12/2000 | Dawson et al. | 435/84 |
| 6,846,656 B1 * | 1/2005 | Koizumi et al. | 435/137 |
| 6,964,858 B2 * | 11/2005 | Koizumi et al. | 435/41 |
| 2003/0109007 A1 * | 6/2003 | Koizumi et al. | 435/84 |

FOREIGN PATENT DOCUMENTS

| | | |
|---|---|---|
| EP | 1 081 230 | 3/2001 |
| EP | 1 154 018 | 11/2001 |
| JP | 3-143387 | 6/1991 |
| JP | 9-285294 | 11/1997 |
| JP | 10-004961 | 1/1998 |
| JP | 10-248588 | 9/1998 |

* cited by examiner

*Primary Examiner*—Herbert J. Lilling
(74) *Attorney, Agent, or Firm*—Fitzpatrick, Cella, Harper & Scinto

(57) ABSTRACT

In the process for producing N-acetylneuraminic acid by using a microorganism having the ability to produce N-acetylneuraminic acid, the present invention provides economical and efficient process for producing N-acetylneuraminic acid by using a microorganism in which the activity to decompose N-acetylneuraminic acid is lost or reduced compared with a wild-type strain.

4 Claims, 1 Drawing Sheet

PROCESS FOR PRODUCING N-ACETYLNEURAMINIC ACID

TECHNICAL FIELD

The present invention relates to a process for producing N-acetylneuraminic acid by using a microorganism in which the activity to decompose N-acetylneuraminic acid is lost or reduced compared with a wild-type strain.

BACKGROUND ART

N-acetylneuraminic acid is known to be produced by extraction or decomposition, and by using enzymes or microorganisms.

An example of a known method by extraction is extraction from a nest of sea swallows, etc. [Carbohydr. Res., 56, 423 (1977)].

An example of a known method by decomposition is decomposition of colominic acid which is an N-acetylneuraminic acid polymer produced by *Escherichia coli*, etc. [J. Biochem., 82, 1425 (1977)].

Known methods utilizing enzymes include: methods using N-acetylneuraminic acid aldolase, pyruvic acid and N-acetylmannosamine [J. Am. Chem. Soc., 110, 6481 (1988); J. Am. Chem. Soc. 110, 7159 (1988)], methods using N-acetylneuraminic acid aldolase, pyruvic acid and N-acetylglucosamine under alkaline conditions [Enzyme Microbiol. Technol., 20, 393 (1997); U.S. Pat. No. 5,665, 574], methods using N-acetylneuraminic acid aldolase, N-acetylglucosamine 2-epimerase, pyruvic acid and N-acetylglucosamine [Angew. Chem. Int. Ed. Eng., 30, 827 (1991); Carbohydr. Res., 306, 575 (1998)]; and methods using N-acetylneuraminic acid synthase, phosphoenolpyruvic acid and N-acetylmannosamine [Japanese Published Unexamined Patent Application No. 4961/98; Glycobiology, 7, 697 (1997)].

An example of a known method using microorganisms is a method utilizing microorganisms which have the ability to produce proteins having N-acetylneuraminic acid aldolase, N-acetylneuraminic acid synthase and N-acetylglucosamine 2-epimerase activities (Japanese Published Unexamined Patent Application No. 136982/01).

However, except the method utilizing microorganisms, the above methods for producing N-acetylneuraminic acid require complicated operations or expensive materials, or involve insufficient conversion efficiency.

Furthermore, further development of an economical and efficient method for producing N-acetylneuraminic acid is desired with respect to the method utilizing microorganisms.

DISCLOSURE OF THE INVENTION

An object of the present invention is to provide an economical and more efficient method for producing N-acetylneuraminic acid.

The present invention relates to the following (1) to (14).

(1) A process for producing N-acetylneuraminic acid which comprises: culturing a microorganism which has the ability to produce N-acetylneuraminic acid and in which the activity to decompose N-acetylneuraminic acid is lost or reduced compared with a wild-type strain in a medium; allowing N-acetylneuraminic acid to form and accumulate in the medium; and recovering N-acetylneuraminic acid from the medium.

(2) A process for producing N-acetylneuraminic acid which comprises: allowing an enzyme source and a precursor of N-acetylneuraminic acid to be present in an aqueous medium, said enzyme source being a culture of a microorganism which has the ability to produce N-acetylneuraminic acid from a precursor of N-acetylneuraminic acid and in which the activity to decompose N-acetylneuraminic acid is lost or reduced compared with a wild-type strain or a treated matter of the culture; allowing N-acetylneuraminic acid to form and accumulate in the aqueous medium; and recovering N-acetylneuraminic acid from the aqueous medium.

(3) The process according to the above (2), wherein the precursor of N-acetylneuraminic acid is N-acetylmannosamine or N-acetylglucosamine.

(4) A process for producing N-acetylneuraminic acid which comprises:
allowing a culture of a microorganism which has the ability to produce a protein having N-acetylneuraminic acid synthase activity and the ability to produce phosphoenolpyruvic acid and in which the activity to decompose N-acetylneuraminic acid is lost or reduced compared with a wild-type strain or a treated matter of the culture as an enzyme source,
N-acetylmannosamine, and
a carbon source required by the microorganism for the production of phosphoenolpyruvic acid
to be present in an aqueous medium;
allowing N-acetylneuraminic acid to form and accumulate in the aqueous medium; and
recovering N-acetylneuraminic acid from the aqueous medium.

(5) A process for producing N-acetylneuraminic acid which comprises:
allowing a culture of microorganism A which has the ability to produce a protein having N-acetylneuraminic acid synthase activity or a treated matter of the culture and a culture of microorganism B having the ability to produce phosphoenolpyruvic acid or a treated matter of the culture as enzyme sources, either one or both of said microorganisms A and B losing the activity to decompose N-acetylneuraminic acid or having the activity to decompose N-acetylneuraminic acid reduced compared with a wild-type strain,
N-acetylmannosamine, and
a carbon source required by the microorganism for the production of phosphoenolpyruvic acid
to be present in an aqueous medium;
allowing N-acetylneuraminic acid to form and accumulate in the aqueous medium; and
recovering N-acetylneuraminic acid from the aqueous medium.

(6) A process for producing N-acetylneuraminic acid which comprises:
allowing a culture of a microorganism which has the ability to produce a protein having N-acetylneuraminic acid synthase activity, the ability to produce a protein having N-acetylglucosamine 2-epimerase activity and the ability to produce phosphoenolpyruvic acid and in which the activity to decompose N-acetylneuraminic acid is lost or reduced compared with a wild-type strain or a treated matter of the culture as an enzyme source,
N-acetylglucosamine, and
a carbon source required by the microorganism for the production of phosphoenolpyruvic acid
to be present in an aqueous medium;
allowing N-acetylneuraminic acid to form and accumulate in the aqueous medium; and recovering N-acetylneuraminic acid from the aqueous medium.

(7) A process for producing N-acetylneuraminic acid which comprises:
allowing a culture of microorganism C having one or two abilities selected from the group consisting of [1] the ability to produce a protein having N-acetylneuraminic acid synthase activity, [2] the ability to produce a protein having N-acetylglucosamine 2-epimerase activity and [3] the ability to produce phosphoenolpyruvic acid or a treated matter of the culture and a culture of microorganism D having all the abilities selected from [1] to [3] that are not possessed by the microorganism C or a treated matter of the culture as enzyme sources, either one or both of said microorganisms C and D losing the activity to decompose N-acetylneuraminic acid or having the activity to decompose N-acetylneuraminic acid reduced compared with a wild-type strain,
N-acetylglucosamine, and
a carbon source required by the microorganism having the ability to produce phosphoenolpyruvic acid for the production of phosphoenolpyruvic acid
to be present in an aqueous medium;
allowing N-acetylneuraminic acid to form and accumulate in the aqueous medium; and
recovering N-acetylneuraminic acid from the aqueous medium.

(8) A process for producing N-acetylneuraminic acid which comprises:
allowing a culture of microorganism E which has the ability to produce a protein having N-acetylneuraminic acid synthase activity or a treated matter of the culture, a culture of microorganism F which has the ability to produce a protein having N-acetylglucosaniine 2-epimerase activity or a treated matter of the culture and a culture of microorganism G having the ability to produce phosphoenolpyruvic acid or a treated matter of the culture as enzyme sources, at least one of said microorganisms losing the activity to decompose N-acetylneuraminic acid or having the activity to decompose N-acetylneuraminic acid reduced compared with a wild-type strain, N-acetylglucosamine, and
a carbon source required by the microorganism having the ability to produce phosphoenolpyruvic acid for the production of phosphoenolpyruvic acid
to be present in an aqueous medium;
allowing N-acetylneuraminic acid to form and accumulate in the aqueous medium; and
recovering N-acetylneuraminic acid from the aqueous medium.

(9) The process according to the above (6) to (8), wherein the carbon source required for the production of phosphoenolpyruvic acid is glucose or fructose.

(10) The process according to the above (1) to (9), wherein the microorganism in which the activity to decompose N-acetylneuraminic acid is lost or reduced compared with a wild-type strain is a microorganism in which sialic acid aldolase activity is lost or reduced compared with a wild-type strain.

(11) The process according to the above (1) to (10), wherein the microorganism is selected from the group consisting of microorganisms belonging to the genera *Escherichia, Corynebacterium* and *Bacillus*.

(12) The process according to the above (11), wherein the microorganism belonging to the genus *Escherichia* is *Escherichia coli* NAN8-71 (FERM BP-7908) in which the activity to decompose N-acetylneuraminic acid is reduced compared with a wild-type strain.

(13) The process according to the above (1) to (12), wherein the treated matter of the culture is concentrated culture, dried culture, cells obtained by centrifuging the culture, a product obtained by subjecting the cells to drying, freeze-drying, treatment with a surfactant, ultrasonication, mechanical friction, treatment with a solvent, enzymatic treatment, protein fractionation or immobilization, or an enzyme preparation obtained by extracting the cells.

(14) *Escherichia coli* NAN8-71 (FERM BP-7908) in which the activity to decompose N-acetylneuraminic acid is reduced compared with a wild-type strain.

The microorganism which has the ability to produce N-acetylneuraminic acid and in which the activity to decompose N-acetylneuraminic acid is lost or reduced compared with a wild-type strain used in the process of the present invention may be any microorganism which is capable of producing N-acetylneuraminic acid and in which the activity to decompose N-acetylneuraminic acid is lost or reduced compared with a wild-type strain. They can be obtained from microorganisms having the ability to produce N-acetylneuraminic acid or, otherwise, from those in which the activity to decompose N-acetylneuraminic acid is lost or reduced compared with a wild-type strain.

Any microorganisms having the ability to produce N-acetylneuraminic acid may be used. Examples of the microorganisms are those known to contain N-acetylneuraminic acid in the component of sugar chain present in the cellular surface layer of the microorganisms [e.g., Adv. Microbiol. Physiol., 35, 135-246 (1993)] and include those belonging to the genus *Escherichia, Corynebacterium* or *Bacillus*.

Examples of the microorganisms belonging to the genus *Escherichia* are those of the species *Escherichia coli*, examples of those belonging to the genus *Corynebacterium* are those of the species *Corynebacterium ammoniagenes* and *Corynebacterium glutamicum*, and examples of those belonging to the genus *Bacillus* are those of the species *Bacillus subtilis*.

As the microorganism having the ability to produce N-acetylneuraminic acid used in the process of the present invention, those with the enzyme activity concerned in the biosynthesis of N-acetylneuraminic acid enhanced by recombinant DNA techniques are preferred.

Specific examples of the microorganisms include those with expression of one or more genes selected from N-acetylneuraminic acid synthase gene, N-acetylglucosamine 2-epimerase gene, etc. enhanced by recombinant DNA techniques.

Examples of N-acetylneuraminic acid synthase genes include neuB gene derived from *Escherichia coli* [J. Bacteriol., 177, 312 (1995)], a gene derived from *Neisseria meningitidis* [Mol. Microbiol., 14, 141 (1994)] and a gene derived from *Campylobacter jejuni* [Mol. Microbiol., 35, 1120 (2000)].

Examples of N-acetylglucosamine 2-epimerase genes include age gene derived from pig (U.S. Pat. No. 5,795,767) and slr1975 derived from a microorganism belonging to the genus *Synechocystis* (WO 00/47730).

Examples of the microorganisms with N-acetylneuraminic acid synthase activity enhanced by recombinant DNA techniques are those carrying a recombinant DNA comprising neuB gene derived from *Escherichia coli*, and a specific example is *Escherichia coli* NM522/pYP18 (FERM BP-7283, Japanese Published Unexamined Patent Application No. 136982/01).

Examples of the microorganisms with N-acetylglucosamine 2-epimerase activity enhanced by recombinant DNA techniques are those carrying a recombinant DNA comprising age gene derived from pig or slr1975 gene derived from a microorganism belonging to the genus *Synechocystis*, and specific examples are *Escherichia coli* XL1-Blue/pEPI1 [J. Biol. Chem., 271, 16294 (1996)] and *Escherichia coli* NM522/pYP16 (FERM BP-7282, Japanese Published Unexamined Patent Application No. 136982/01).

The microorganisms in which the activity to decompose N-acetylneuraminic acid is lost or reduced compared with a wild-type strain can be obtained by giving an ordinary mutagenesis to a parent strain, spreading the treated cells on an agar plate medium containing N-acetylneuraminic acid as a sole carbon source or nitrogen source and selecting strains incapable of growing or showing delayed growth compared with the parent strain subjected to the mutagenesis. Examples of the parent strains are wild-type strains and mutants in which the activity to decompose N-acetylneuraminic acid is reduced compared with wild-type strains.

For the purpose of the present invention, "a wild-type strain" means a microorganism of the type that is most frequently observed in the species to which the microorganism belongs in the natural population. "A parent strain" means a strain that has been subjected to mutagenesis to obtain the microorganism in which the activity to decompose N-acetylneuraminic acid is lost or reduced compared with a wild-type strain, or a strain subjected to transformation using recombinant DNA techniques.

The microorganisms in which the activity to decompose N-acetylneuraminic acid is lost or reduced compared with a wild-type strain can be obtained, for example; by giving, to a microorganism as a parent strain, an ordinary mutagenesis (A Short Course in Bacterial Genetics), for example, treatment with a mutagenic agent such as N-methyl-N'-nitro-N-nitrosoguanidine, or mutagenesis with UV irradiation or γ-ray irradiation; properly diluting the resulting cells with buffer; spreading the cells on an agar plate medium containing N-acetylneuraminic acid as a sole carbon source or nitrogen source; and selecting a strain showing delayed growth compared with the parent strain subjected to the mutagenesis or incapable of growing as the desired mutant strain.

The microorganisms in which the activity to decompose N-acetylneuraminic acid is lost or reduced compared with a wild-type strain can also be obtained by a known method of mutagenesis utilizing homologous recombination on chromosome or through gene disruption techniques (Molecular Cloning, Third Edition or A Short Course in Bacterial Genetics). Sialic acid aldolase is known as an N-acetylneuraminic acid-decomposing enzyme, and a gene encoding the enzyme has been identified.

As sialic acid aldolase derived from *Escherichia coli*, the protein having the amino acid sequence shown in SEQ ID NO: 3 is known, and DNA having the nucleotide sequence shown in SEQ ID NO: 4 is known as DNA encoding the protein.

More specifically, the microorganisms in which the activity to decompose N-acetylneuraminic acid is lost or reduced compared with a wild-type strain can be obtained by mutagenesis utilizing homologous recombination on chromosome or through gene disruption techniques according to methods utilizing a microorganism that expresses a group of recombinant proteins derived from λ phage (Red recombination system) [Gene, 246, 321-330 (2000); Proc. Nat. Acad. Sci., 97, 6640-6645 (2000)].

When *Escherichia coli* is used as the microorganism, for example, *Escherichia coli* losing sialic acid aldolase activity can be obtained by transforming *Escherichia coli* KM22 expressing Red recombination system 8 [J. Bacteriol., 180, 2063 (1998)]or *Escherichia coli* transformed or transduced with a gene participating in λred recombination system contained in KM22 with:

(1) straight chain DNA comprising a drug resistance gene and carrying, at its both termini, DNAs, said DNAs are the same as those present on the outside of both termini of DNA shown in SEQ ID NO: 4 on chromosomal DNA of *Escherichia coli*;

(2) straight chain DNA carrying, at its both termini, DNAs, said DNAs are the same as those present on the outside of both termini of DNA shown in SEQ ID No: 4 on chromosomal DNA of *Escherichia coli*; or (3) straight chain DNA comprising a drug resistance gene and a gene that can be used for negative selection and carrying, at its both termini, DNAs, said DNAs are the same as those present on the outside of both termini of DNA shown in SEQ ID No: 4 on chromosomal DNA of *Escherichia coli*.

As the drug resistance gene, any drug resistance genes that impart resistance to a drug to which the host microorganism show sensitivity can be used. When *Escherichia coli* is used as the microorganism, examples of the drug resistance genes are kanamycin resistance gene, chloramphenicol resistance gene, gentamicin resistance gene, spectinomycin resistance gene, tetracycline resistance gene and ampicillin resistance gene.

A gene that can be used for negative selection means a gene that is fatal to a host microorganism under certain culture conditions when the gene is expressed in the host microorganism. Examples of the genes are sacB gene derived from a microorganism belonging to the genus *Bacillus* [Appl. Environ. Microbiol., 59, 1361-1366 (1993)] and rpsL gene derived from a microorganism belonging to the genus *Escherichia* [Genomics, 72, 99-104 (2001)].

On the above-mentioned straight chain DNA, the DNAs on the both termini of the straight chain DNA are located in the same direction as the DNAs on the outside of the both termini of DNA shown in SEQ ID No: 4 are located on chromosomal DNA of *Escherichia coli*, and the length is preferably about 500 bp to 5 Kbp, more preferably about 500 bp to 2 kbp and most preferably about 1 kbp.

The above-mentioned straight chain DNA fragments can be prepared by PCR. The desired straight chain DNA can also be obtained by constructing DNA containing the above-mentioned straight chain DNA on plasmid and then carrying out a treatment with restriction enzymes.

Specific examples of the methods to obtain *Escherichia coli* losing sialic acid aldolase activity by using the straight chain DNAs of the above (1) to (3) are:

Method 1: a method which comprises introducing the straight chain DNA of the above (1) into *Escherichia coli* and selecting a transformant carrying the straight chain DNA inserted on its chromosomal DNA by homologous recombination using drug resistance as a marker;

Method 2: a method which comprises introducing the straight chain DNA of the above (2) into the transformant obtained according to the above method 1 and eliminating the drug resistance gene inserted into its chromosomal DNA according to the method; and Method 3: a method which comprises:

[1] introducing the straight chain DNA of the above (3) into *Escherichia coli* and selecting a transformant carrying the straight chain DNA inserted into its chromosomal DNA by homologous recombination using drug resistance as a marker;

[2] synthesizing DNA by ligation of DNAs located on the outside of both termini of DNA having the nucleotide sequence shown in SEQ ID NO: 4 on the chromosomal DNA in the same direction as that on the chromosomal DNA and introducing the thus synthesized DNA into the transformant obtained in the above [1]; and

[3] culturing the transformant subjected to the operation of the above [2] under the conditions under which the gene that can be used for negative selection is expressed and selecting a strain capable of growing by the culturing as a strain in which the drug resistance gene and the gene usable for negative selection are eliminated from the chromosomal DNA.

Any method to introduce DNA into a host microorganism can be used for the introduction of the straight chain DNA into the host microorganism in the above methods. For example, the method using calcium ion [Proc. Natl. Acad. Sci., USA 69, 2110 (1972)], the protoplast method (Japanese Published Unexamined Patent Application No. 248394/88) and electroporation [Nucleic Acids Res., 16, 6127 (1988) can be used.

The above methods 2 and 3 are methods that leave no foreign genes such as a drug resistance gene and a gene usable for negative selection on the chromosomal DNA of the transformant to be finally obtained.

The above-described methods to obtain microorganisms in which the activity to decompose N-acetylneuraminic acid is lost are methods in which the gene coding for a protein having the activity to decompose sialic acid on the chromosomal DNA is completely eliminated. It is also possible to obtain Escherichia coli losing the activity to decompose N-acetylneuraminic acid by using, in the straight chain DNAs of the above (1) and (3) used in the above methods, straight chain DNA carrying DNAs comprising DNAs at the 5'- and 3'-termini of the DNA having the nucleotide sequence shown in SEQ ID No: 4 at its both termini in place of DNAs present on the outside of both termini of DNA shown in SEQ ID NO: 4 on the chromosomal DNA.

An example of the microorganism in which the activity to decompose N-acetylneuraminic acid is reduced compared with a wild-type strain is Escherichia coli NAN8-71. This strain was deposited with International Patent Organism Depositary, National Institute of Advanced Industrial Science and Technology: Tsukuba Central 6, 1-1, Higashi 1-Chome, Tsukuba-shi, Ibaraki-ken 305-8566 Japan as of Feb. 20, 2002 as FERM BP-7908.

The microorganism which has the ability to produce N-acetylneuraminic acid from a precursor of N-acetylneuraminic acid and in which the activity to decompose N-acetylneuraminic acid is lost or reduced compared with a wild-type strain may be any microorganism which is capable of producing N-acetylneuraminic acid from a precursor of N-acetylneuraminic acid and in which the activity to decompose N-acetylneuraminic acid is lost or reduced compared with a wild-type strain.

Examples of the microorganisms are those belonging to the genus Escherichia, Corynebacterium or Bacillus.

Examples of the microorganisms belonging to the genus Escherichia are those of the species Escherichia coli, examples of the microorganisms belonging to the genus Corynebacterium are those of the species Corynebacterium ammoniagenes and Corynebacterium glutamicum, and examples of the microorganisms belonging to the genus Bacillus are those of the species Bacillus subtilis.

The microorganism which has the ability to produce N-acetylneuraminic acid from a precursor of N-acetylneuraminic acid and in which the activity to decompose N-acetylneuraminic acid is lost or reduced compared with a wild-type strain can be obtained from microorganisms having the ability to produce N-acetylneuraminic acid from a precursor of N-acetylneuraminic acid or, otherwise, from those in which the activity to decompose N-acetylneuraminic acid is lost or reduced compared with a wild-type strain.

The microorganism having the ability to produce N-acetylneuraminic acid from a precursor of N-acetylneuraminic acid may be any microorganisms that are capable of producing N-acetylneuraminic acid from a precursor of N-acetylneuraminic acid. For example, microorganisms capable of producing N-acetylneuraminic acid from N-acetylmannosamine or N-acetylglucosamine can be used.

The precursor of N-acetylneuraminic acid may be any precursors that are converted to N-acetylneuraminic acid by the enzymatic activity possessed by the microorganisms. Preferred examples are N-acetylmannosamine and N-acetylglucosamine.

Examples of the microorganisms capable of producing N-acetylneuraminic acid from N-acetylmannosamine or N-acetylglucosamine are those in which either one or both of N-acetylneuraminic acid synthase activity and N-acetylglucosamine 2-epimerase activity are strong.

Examples of the microorganisms in which either one or both of N-acetylneuraminic acid synthase activity and N-acetylglucosamine 2-epimerase activity are strong are those in which either one or both of these activities are enhanced by recombinant DNA techniques.

Furthermore, examples of the microorganisms in which either one or both of N-acetylneuraminic acid synthase activity and N-acetylglucosamine 2-epimerase activity are strong are those carrying a recombinant DNA comprising either one or both of N-acetylneuraminic acid synthase gene and N-acetylglucosamine 2-epimerase gene. The microorganisms may carry two recombinant DNAs severally comprising N-acetylneuraminic acid synthase gene and N-acetylglucosamine 2-epimerase gene.

Examples of the recombinant DNA comprising N-acetylneuraminic acid synthase gene are pYP18 [prepared from Escherichia coli NM522/pYP18 (FERM BP-7283, Japanese Published Unexamined Patent Application No. 136982/01)], which is a recombinant DNA comprising neuB gene derived from Escherichia coli, and pEPI1 [prepared from Escherichia coli XL1-Blue/pEPI1, J. Biol. Chem., 271, 16294 (1996)] and pYP16 [prepared from FERM BP-7282, Japanese Published Unexamined Patent Application No. 136982/01, etc.], which are recombinant DNAs comprising N-acetylglucosamine 2-epimerase gene.

The microorganisms which have the ability to produce N-acetylneuraminic acid from a precursor of N-acetylneuraminic acid and in which the activity to decompose N-acetylneuraminic acid is lost or reduced compared with a wild-type strain can be obtained by using a microorganism capable of producing N-acetylneuraminic acid from a precursor of N-acetylneuraminic acid as a parent strain and applying the above-described mutagenesis or homologous recombination techniques.

It is also possible to obtain the microorganisms which have the ability to produce N-acetylneuraminic acid from a precursor of N-acetylneuraminic acid and in which the activity to decompose N-acetylneuraminic acid is lost or reduced compared with a wild-type strain by using the above-described Escherichia coli NAN8-71 (FERM BP-7908) in which the activity to decompose N-acetylneuraminic acid is lost or reduced compared with a wild-type strain as a parent strain and introducing either one or both of the above-described recombinant DNA comprising N-acetylneuraminic acid synthase gene and recombinant DNA comprising N-acetylglucosamine 2-epimerase gene into the parent strain.

The microorganism which has the ability to produce a protein having N-acetylneuraminic acid synthase activity used in the present invention may be any microorganisms that are capable of producing a protein having N-acetylneuraminic acid synthase activity.

Examples of the microorganisms are those belonging to the genus *Escherichia*, *Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms which have the ability to produce a protein having N-acetylneuraminic acid synthase activity are those with N-acetylneuraminic acid synthase activity enhanced by mutagenesis or recombinant DNA techniques.

Specific examples of the microorganisms are those obtained by introducing a recombinant DNA comprising N-acetylneuraminic acid synthase gene.

An example of the microorganism carrying a recombinant DNA comprising N-acetylneuraminic acid synthase gene is *Escherichia coli* NM522/pYP18 (FERM BP-7283).

The microorganism which has the ability to produce a protein having N-acetylneuraminic acid synthase activity and in which the activity to decompose N-acetylneuraminic acid is lost or reduced compared with a wild-type strain used in the present invention may be any microorganisms which are capable of producing a protein having N-acetylneuraminic acid synthase activity and in which the activity to decompose N-acetylneuraminic acid is lost or reduced compared with a wild-type strain.

Examples of the microorganisms are those belonging to the genus *Escherichia*, *Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylneuraminic acid synthase activity and in which the activity to decompose N-acetylneuraminic acid is lost or reduced compared with a wild-type strain can be obtained from microorganisms which have the ability to produce a protein having N-acetylneuraminic acid synthase activity or, otherwise, from microorganisms in which the activity to decompose N-acetylneuraminic acid is lost or reduced compared with a wild-type strain.

More specifically, the microorganisms which have the ability to produce a protein having N-acetylneuraminic acid synthase activity and in which the activity to decompose N-acetylneuraminic acid is lost or reduced compared with a wild-type strain can be obtained by using, for example, *Escherichia coli* NM522/pYP18 (FERM BP-7283) in which N-acetylneuraminic acid synthase activity is enhanced as a parent strain and applying the above-described mutagenesis or homologous recombination techniques to the parent strain.

It is also possible to obtain the microorganisms which have the ability to produce a protein having N-acetylneuraminic acid synthase activity and in which the activity to decompose N-acetylneuraminic acid is lost or reduced compared with a wild-type strain by using, for example, *Escherichia coli* NAN8-71 (FERM BP-7908) in which the activity to decompose N-acetylneuraminic acid is lost or reduced compared with a wild-type strain as a parent strain and introducing pYP18, a recombinant DNA comprising N-acetylneuraminic acid synthase gene, into the parent strain.

The microorganism which has the ability to produce a protein having N-acetylglucosamine 2-epimerase activity used in the present invention may be any microorganisms that are capable of producing a protein having N-acetylglucosamine 2-epimerase activity.

Examples of the microorganisms are those belonging to the genus *Escherichia*, *Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms which have the ability to produce a protein having N-acetylglucosamine 2-epimerase activity are those in which N-acetylglucosamine 2-epimerase activity is enhanced by mutagenesis or recombinant DNA techniques.

Specific examples of the microorganisms are those obtained by introducing a recombinant DNA comprising N-acetylglucosamine 2-epimerase gene.

Examples of the microorganisms carrying a recombinant DNA comprising N-acetylglucosamine 2-epimerase gene are *Escherichia coli* XL1-Blue/pEPI1 and *Escherichia coli* NM522/pYP16 (FERM BP-7282).

The microorganism which has the ability to produce a protein having N-acetylglucosamine 2-epimerase activity and in which the activity to decompose N-acetylneuraminic acid is lost or reduced compared with a wild-type strain used in the present invention may be any microorganism which is capable of producing a protein having N-acetylglucosamine 2-epimerase activity and in which the activity to decompose N-acetylneuraminic acid is lost or reduced compared with a wild-type strain.

Examples of the microorganisms are those belonging to the genus *Escherichia*, *Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylglucosamine 2-epimerase activity and in which the activity to decompose N-acetylneuraminic acid is lost or reduced compared with a wild-type strain can be obtained from the microorganisms which have the ability to produce a protein having N-acetylglucosamine 2-epimerase activity or, otherwise, from the microorganisms in which the activity to decompose N-acetylneuraminic acid is lost or reduced compared with a wild-type strain.

More specifically, the microorganisms which have the ability to produce a protein having N-acetylglucosamine 2-epimerase activity and in which the activity to decompose N-acetylneuraminic acid is lost or reduced compared with a wild-type strain can be obtained by using, for example, *Escherichia coli* XL1-Blue/pEPI1 or *Escherichia coli* NM522/pYP16 (FERM BP-7282) in which N-acetylglucosamine 2-epimerase activity is enhanced as a parent strain and applying the above-described mutagenesis or homologous recombination techniques to the parent strain.

It is also possible to obtain the microorganisms which have the ability to produce a protein having N-acetylglucosamine 2-epimerase activity and in which the activity to decompose N-acetylneuraminic acid is lost or reduced compared with a wild-type strain by using, for example, *Escherichia coli* NAN8-71 (FERM BP-7908) in which the activity to decompose N-acetylneuraminic acid is lost or reduced compared with a wild-type strain as a parent strain and introducing pEPI1 or pYP16, a recombinant DNA comprising N-acetylglucosamine 2-epimerase gene, into the parent strain.

The microorganism having the ability to produce phosphoenolpyruvic acid used in the present invention may be any microorganisms that are capable of producing phosphoenolpyruvic acid.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms having the ability to produce phosphoenolpyruvic acid are those in which the ability to produce phosphoenolpyruvic acid is enhanced by mutagenesis or recombinant DNA techniques.

A specific example of the microorganism is *Escherichia coli* W1485lip2 [Biosci. Biotech. Biochem., 58, 2164 (1994)].

The microorganism which has the ability to produce phosphoenolpyruvic acid and in which the activity to decompose N-acetylneuraminic acid is lost or reduced compared with a wild-type strain used in the present invention may be any microorganism which is capable of producing phosphoenolpyruvic acid and in which the activity to decompose N-acetylneuraminic acid is lost or reduced compared with a wild-type strain.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce phosphoenolpyruvic acid and in which the activity to decompose N-acetylneuraminic acid is lost or reduced compared with a wild-type strain can be obtained from the microorganisms having the ability to produce phosphoenolpyruvic acid or, otherwise, from the microorganisms in which the activity to decompose N-acetylneuraminic acid is lost or reduced compared with a wild-type strain.

More specifically, the microorganisms which have the ability to produce phosphoenolpyruvic acid and in which the activity to decompose N-acetylneuraminic acid is lost or reduced compared with a wild-type strain can be obtained by using, for example, *Escherichia coli* W1485lip2 in which the ability to produce phosphoenolpyruvic acid is enhanced as a parent strain and applying the above-described mutagenesis or homologous recombination techniques to the parent strain.

The microorganism which has the ability to produce a protein having N-acetylneuraminic acid synthase activity and the ability to produce a protein having N-acetylglucosamine 2-epimerase activity used in the present invention may be any microorganisms that are capable of producing a protein having N-acetylneuraminate synthasse activity and of producing a protein having N-acetylglucosamine 2-epimerase activity.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms which have the ability to produce a protein having N-acetylneuraminic acid synthase activity and the ability to produce a protein having N-acetylglucosamine 2-epimerase activity are those in which N-acetylneuraminic acid synthase activity and N-acetylglucosamine 2-epimerase activity are enhanced.

Specific examples of the microorganisms are those carrying a recombinant DNA comprising N-acetylneuraminic acid synthase gene and a recombinant DNA comprising N-acetylglucosamine 2-epimerase gene introduced by recombinant DNA techniques.

The microorganisms may carry a recombinant DNA comprising N-acetylneuraminic acid synthase gene and N-acetylglucosamine 2-epimerase gene simultaneously.

More specifically, the microorganisms obtained by introducing pYP18, a recombinant DNA comprising N-acetylneuraminic acid synthase gene, and pEPI1 or pYP16, a recombinant DNA comprising N-acetylglucosamine 2-epimerase gene, can be used.

The microorganism which has the ability to produce a protein having activity and the ability to produce a protein having N-acetylglucosamine 2-epimerase activity and in which the activity to decompose N-acetylneuraminic acid is lost or reduced compared with a wild-type strain used in the present invention may be any microorganism which is capable of producing a protein having N-acetylneuraminic acid synthase activity and of producing a protein having N-acetylglucosamine 2-epimerase activity and in which the activity to decompose N-acetylneuraminic acid is lost or reduced compared with a wild-type strain.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylneuraminic acid synthase activity and the ability to produce a protein having N-acetylglucosamine 2-epimerase activity and in which the activity to decompose N-acetylneuraminic acid is lost or reduced compared with a wild-type strain can be obtained from the microorganisms which have the ability to produce a protein having N-acetylneuraminic acid synthase activity and the ability to produce a protein having N-acetylglucosamine 2-epimerase activity, or otherwise, from the microorganisms in which the activity to decompose N-acetylneuraminic acid is lost or reduced compared with a wild-type strain.

Examples of the microorganisms which have the ability to produce a protein having N-acetylneuraminic acid synthase activity and the ability to produce a protein having N-acetylglucosamine 2-epimerase activity are those obtained by introducing pYP18, a recombinant DNA comprising N-acetylneuraminic acid synthase gene, and pEPI1 or pYP16, a recombinant DNA comprising N-acetylglucosamine 2-epimerase gene, into a host microorganism.

The microorganisms which have the ability to produce a protein having N-acetylneuraminic acid synthase activity and the ability to produce a protein having N-acetylglucosamine 2-epimerase activity and in which the activity to decompose N-acetylneuraminic acid is lost or reduced compared with a wild-type strain can be obtained by using a microorganism which has the ability to produce a protein having N-acetylneuraminic acid synthase activity and the ability to produce a protein having N-acetylglucosamine 2-epimerase activity obtained according to the above method as a parent strain and applying the above-described mutagenesis or homologous recombination techniques to the parent strain.

It is also possible to obtain the microorganisms which have the ability to produce a protein having N-acetylneuraminic acid synthase activity and the ability to produce a protein having N-acetylglucosamine 2-epimerase activity and in which the activity to decompose N-acetylneuraminic acid is lost or reduced compared with a wild-type strain by using, for example, *Escherichia coli* NAN8-71 (FERM BP-7908) in which the activity to decompose N-acetylneuraminic acid is lost or reduced compared with a wild-type strain as a parent strain and introducing pYP18, a recombinant DNA comprising N-acetylneuraminic acid synthase gene, and pEPI1 or pYP16, a recombinant DNA comprising N-acetylglucosamine 2-epimerase gene, into the parent strain.

The microorganism which has the ability to produce a protein having N-acetylglucosamine 2-epimerase activity and the ability to produce phosphoenolpyruvic acid used in the present invention may be any microorganisms that are capable of producing a protein having N-acetylglucosamine 2-epimerase activity and of producing phosphoenolpyruvic acid.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms which have the ability to produce a protein having N-acetylglucosamine 2-epimerase activity and the ability to produce phosphoenolpyruvic acid are those in which N-acetylglucosamine 2-epimerase activity and the ability to produce phosphoenolpyruvic acid are enhanced.

Specific examples of the microorganisms are those carrying a recombinant DNA comprising N-acetylglucosamine 2-epimerase gene introduced by recombinant DNA techniques with the ability to produce phosphoenolpyruvic acid enhanced by mutagenesis or recombinant DNA techniques.

More specifically, the microorganisms obtained by introducing pEPI1 or pYP16, a recombinant DNA comprising N-acetylglucosamine 2-epimerase gene, into *Escherichia coli* W1485lip2, a microorganism with its ability to produce phosphoenolpyruvic acid enhanced, can be used.

The microorganisms which have the ability to produce a protein having N-acetylglucosamine 2-epimerase activity and the ability to produce phosphoenolpyruvic acid can be obtained by using a microorganism which has the ability to produce a protein having N-acetylglucosamine 2-epimerase activity and the ability to produce phosphoenolpyruvic acid obtained according to the above method as a parent strain and applying the above-described mutagenesis or homologous recombination techniques to the parent strain.

The microorganism which has the ability to produce a protein having N-acetylglucosamine 2-epimerase activity and the ability to produce phosphoenolpyruvic acid and in which the activity to decompose N-acetylneuraminic acid is lost or reduced compared with a wild-type strain used in the present invention may be any microorganism which is capable of producing a protein having N-acetylglucosamine 2-epimerase activity and of producing phosphoenolpyruvic acid and in which the activity to decompose N-acetylneuraminic acid is lost or reduced compared with a wild-type strain.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylglucosamine 2-epimerase activity and the ability to produce phosphoenolpyruvic acid and in which the activity to decompose N-acetylneuraminic acid is lost or reduced compared with a wild-type strain can be obtained from the microorganisms which have the ability to produce a protein having N-acetylglucosamine 2-epimerase activity and the ability to produce phosphoenolpyruvic acid, or otherwise, from the microorganisms in which the activity to decompose N-acetylneuraminic acid is lost or reduced compared with a wild-type strain.

Examples of the microorganisms which have the ability to produce a protein having N-acetylglucosamine 2-epimerase activity and the ability to produce phosphoenolpyruvic acid are those obtained by introducing pEPI1 or pYP16, a recombinant DNA comprising N-acetylglucosamine 2-epimerase gene, into the above-mentioned *Escherichia coli* W1485lip2, a microorganism in which the ability to produce phosphoenolpyruvic acid is enhanced.

The microorganisms which have the ability to produce a protein having N-acetylglucosamine 2-epimerase activity and the ability to produce phosphoenolpyruvic acid and in which the activity to decompose N-acetylneuraminic acid is lost or reduced compared with a wild-type strain can be obtained by using a microorganism capable of producing a protein having N-acetylglucosamine 2-epimerase activity and of producing phosphoenolpyruvic acid obtained according to the above method as a parent strain and applying the above-described mutagenesis or homologous recombination techniques to the parent strain.

The microorganism which has the ability to produce a protein having N-acetylneuraminic acid synthase activity and the ability to produce phosphoenolpyruvic acid used in the present invention may be any microorganisms that are capable of producing a protein having N-acetylneuraminic acid synthase activity and of producing phosphoenolpyruvic acid.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

Preferred examples of the microorganisms which have the ability to produce a protein having N-acetylneuraminic acid synthase activity and the ability to produce phosphoenolpyruvic acid are those in which N-acetylneuraminic acid synthase activity and the ability to produce phosphoenolpyruvic acid are enhanced.

Specific examples of the microorganisms are those carrying a recombinant DNA comprising N-acetylneuraminic acid synthase gene introduced by recombinant DNA techniques with the ability to produce phosphoenolpyruvic acid enhanced by mutagenesis or recombinant DNA techniques.

More specifically, the microorganisms obtained by introducing pYP18, a recombinant DNA comprising N-acetylneuraminic acid synthase gene, into *Escherichia coli* W1485lip2, a microorganism in which the ability to produce phosphoenolpyruvic acid is enhanced, can be used.

The microorganism which has the ability to produce a protein having N-acetylneuraminic acid synthase activity and the ability to produce phosphoenolpyruvic acid and in which the activity to decompose N-acetylneuraminic acid is lost or reduced compared with a wild-type strain used in the present invention may be any microorganism which is capable of producing a protein having N-acetylneuraminic acid synthase activity and of producing phosphoenolpyruvic acid and in which the activity to decompose N-acetylneuraminic acid is lost or reduced compared with a wild-type strain.

Examples of the microorganisms are those belonging to the genus *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylneuraminic acid synthase activity and the ability to produce phosphoenolpyruvic acid and in which the activity to decompose N-acetylneuraminic acid is lost or reduced compared with a wild-type strain can be obtained from the microorganisms which have the ability to produce a protein having N-acetylneuraminic acid synthase activity and the ability to produce phosphoenolpyruvic acid, or otherwise, from those in which the activity to decompose N-acetylneuraminic acid is lost or reduced compared with a wild-type strain.

Examples of the microorganisms which have the ability to produce a protein having N-acetylneuraminic acid synthase activity and the ability to produce phosphoenolpyruvic acid are those obtained by introducing pYP18, a recombinant DNA comprising N-acetylneuraminic acid synthase gene, into the above-mentioned *Escherichia coli* W1485lip2, a microorganism in which the ability to produce phosphoenolpyruvic acid is enhanced.

The microorganisms which have the ability to produce a protein having N-acetylneuraminic acid synthase activity and the ability to produce phosphoenolpyruvic acid and in which the activity to decompose N-acetylneuraminic acid is lost or reduced compared with a wild-type strain can be obtained by using the above-mentioned microorganism capable of producing a protein having N-acetylneuraminic acid synthase activity and of producing phosphoenolpyruvic acid as a parent strain and applying the above-described mutagenesis or homologous recombination techniques to the parent strain.

The microorganism which has the ability to produce a protein having N-acetylneuraminic acid synthase activity, the ability to produce a protein having N-acetylglucosamine 2-epimerase activity and the ability to produce phosphoenolpyruvic acid and in which the activity to decompose N-acetylneuraminic acid is lost or reduced compared with a wild-type strain used in the present invention may be any microorganism which is capable of producing a protein having N-acetylneuraminic acid synthase activity, of producing a protein having N-acetylglucosamine 2-epimerase activity and of producing phosphoenolpyruvic acid and in which the activity to decompose N-acetylneuraminic acid is lost or reduced compared with a wild-type strain.

Examples of the microorganisims are those belonging to the *Escherichia, Corynebacterium* or *Bacillus*.

Examples of the microorganisms belonging to the genus *Escherichia* are those of the species *Escherichia coli*, examples of the microorganisms belonging to the genus *Corynebacterium* are those of the species *Corynebacterium ammoniagenes* and *Corynebacterium glutamicum*, and examples of the microorganisms belonging to the genus *Bacillus* are those of the species *Bacillus subtilis*.

The microorganisms which have the ability to produce a protein having N-acetylneuraminic acid synthase activity, the ability to produce a protein having N-acetylglucosamine 2-epimerase activity and the ability to produce phosphoenolpyruvic acid and in which the activity to decompose N-acetylneuraminic acid is lost or reduced compared with a wild-type strain can be obtained from the microorganisms which have the ability to produce a protein having synthase N-acetylneuraminic acid synthase activity, the ability to produce a protein having N-acetylglucosamine 2-epimerase activity and the ability to produce phosphoenolpyruvic acid, or otherwise, from those in which the activity to decompose N-acetylneuraminic acid is lost or reduced compared with a wild-type strain.

Preferred examples of the microorganisms which have the ability to produce a protein having N-acetylneuraminic acid synthase activity, the ability to produce a protein having N-acetylglucosamine 2-epimerase activity and the ability to produce phosphoenolpyruvic acid are those in which N-acetylneuraminic acid synthase activity, N-acetylglucosamine 2-epimerase activity and the ability to produce phosphoenolpyruvic acid are enhanced.

Specific examples of the microorganisms are those carrying a recombinant DNA comprising N-acetylneuraminic acid synthase gene and a recombinant DNA comprising N-acetylglucosamime 2-epimerase gene introduced according to recombinant DNA techniques with the ability to produce phosphoenolpyruvic acid enhanced by mutagenesis or recombinant DNA techniques. The microorganisms may carry a recombinant DNA simultaneously comprising N aectylneuraminate synthase N-acetylneuraminic acid synthase gene and N-acetylglucosamine 2-epimerase gene with the ability to produce phosphoenoipyruvic acid enhanced.

Examples of the microorganisms are those obtained by introducing pYP18, a recombinant DNA comprising N-acetylneuraminic acid synthase gene, and pEPI1 or pYP16, a recombinant DNA comprising N-acetylglucosamine 2-epimerase gene, into *Escherichia coli* W1485lip2, a microorganism in which the ability to produce phosphoenolpyruvic acid is enhanced.

The microorganisms which have the ability to produce a protein having N-acetylneuraminic acid synthase activity, the ability to produce a protein having N-acetylglucosamine 2-epimerase activity and the ability to produce phosphoenolpyruvic acid and in which the activity to decompose N-acetylneuraminic acid is lost or reduced compared with a wild-type strain can be obtained by using a microorganism which has the ability to produce a protein having N-acetylneuraminic acid synthase activity, the ability to produce a protein having N-acetylglucosamine 2-epimerase activity and the ability to produce phosphoenolpyruvic acid obtained according to the above method as a parent strain and applying the above-described mutagenesis or homologous recombination techniques to the parent strain.

In the process of the present invention, when a microorganism constructed by using recombinant DNA techniques is used, various gene manipulating operations such as isolation and purification of plasmid DNA, preparation of recombinant DNA, transformation with the recombinant DNA and polymerase chain reaction (hereinafter referred to as PCR) can be carried out according to known methods (Molecular Cloning, Third Edition or Current Protocols in Molecular Biology).

Proteins concerned in the production of N-acetylneuraminic acid such as N-acetylneuraminic acid synthase and N-acetylglucosamine 2-epimerase can be expressed in a microorganism by using recombination techniques: that is, by preparing a DNA fragment of an appropriate length containing the region coding for the protein; preparing recombinant DNA by inserting the DNA fragment into an appropriate expression vector at a site downstream of the promoter; and introducing the recombinant DNA into a microorganism suited for the expression vector.

Any microorganism that can express a desired gene can be used.

The expression vectors used are those capable of autonomous replication or integration into the chromosomal DNA in the above microorganisms and comprising a promoter at a position appropriate for the transcription of DNA coding for the protein.

When a prokaryote such as bacteria is used as the microorganism, it is preferred that the recombinant DNA comprising DNA coding for the protein concerned in the production of N-acetylneuraminic acid is capable of autonomous replication in the prokaryote and is a vector comprising a promoter, a ribosome binding sequence, DNA coding for the protein and a transcription termination sequence. The recombinant DNA may further comprise a gene regulating the promoter.

Examples of suitable expression vectors are pHelix1 (Roche Diagnostics), pKK233-2 (Amersham Pharmacia Biotech), pSE280 (Invitrogen), pGEMEX-1 (Promega), pQE-8 (QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+) (Stratagene), pTrs30 [prepared from *Escherichia coli* JM109/pTrS30 (FERM BP-5407), pTrs32 [prepared from *Escherichia coli* JM109/pTrS32 (FERM BP-5408)], pPAC31 (WO98/12343), pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (Amersham Pharmacia Biotech) and pET system (Novagen).

As the promoter, any promoters capable of functioning in host cells can be used. For example, promoters derived from *Escherichia coli* or phage, such as trp promoter (Ptrp), lac promoter, $P_L$ promoter, $P_R$ promoter and T7 promoter can be used. Artificially modified promoters such as a promoter in which two Ptrp are combined in tandem (Ptrp×2), tac promoter, lacT7 promoter and letI promoter can also be used.

It is preferred to use a plasmid in which the distance between the Shine-Dalgarno sequence i.e., ribosome binding sequence, and the initiation codon is adjusted to an appropriate length (e.g., 6-18 bases).

In the recombinant DNA used in the process of the present invention, the transcription termination sequence is not essential for the expression of the DNA coding for the desired protein, but it is preferred that the transcription termination sequence lie immediately downstream of the structural gene.

Examples of suitable host cells are microorganisms belonging to the genera *Escherichia, Serratia, Bacillus, Brevibacterium, Corynebacterium, Microbacterium* and *Pseudomonas*, specifically, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NM522, *Escherichia coli* NY49, *Escherichia coli* GI698, *Escherichia coli* TB1, *Serratia ficaria, Serratia fonticola, Serratia liquefaciens, Serratia marcescens, Bacillus subtilis, Bacillus amyloliquefaciens, Corynebacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC13869, *Corynebacterium acetoacidophilum* ATCC13870, *Microbacterium ammoniaphilum* ATCC15354, *Pseudomonas putida* and *Pseudomonas* sp. D-0110.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and the method described in Gene, 17, 107 (1982) or Mol. Gen. Genet., 168, 111 (1979).

Culturing of the microorganisms used in the process of the present invention can be carried out by the conventional method described below.

For the culturing of the microorganism used in the process of the present invention, any of natural media and synthetic media can be used insofar as it contains carbon sources, nitrogen sources, inorganic salts, etc. that can be assimilated by the microorganism and is a medium suitable for efficient culturing of the transformant.

As the carbon sources, any carbon sources that can be assimilated by the microorganism may be used. For examples, carbohydrates such as glucose, fructose, sucrose, molasses containing them, starch and starch hydrolyzate, organic acids such as acetic acid and propionic acid, and alcohols such as ethanol and propanol can be used.

As the nitrogen sources, ammonia, ammonium salts of inorganic or organic acids such as ammonium chloride, ammonium sulfate, ammonium acetate and ammonium phosphate, peptone, meat extract, yeast extract, corn steep liquor, casein hydrolyzate, soybean cake, soybean cake hydrolyzate, various fermented cells and digested products thereof can be used.

As the inorganic salts, potassium dihydrogenphosphate, dipotassium hydrogenphosphate, magnesium phosphate, magnesium sulfate, sodium chloride, ferrous sulfate, manganese sulfate, copper sulfate and calcium carbonate can be used.

Culturing is carried out under aerobic conditions, for example, by shaking culture or submerged spinner culture under aeration. Culturing temperature is preferably 15-40° C. and culturing period is usually 16 hours to 7 days. It is preferred that the pH is maintained at 3.0-9.0 during the culturing. The pH adjustment is carried out by using an inorganic or organic acid, an alkali solution, urea, calcium carbonate, ammonia, etc.

If necessary, antibiotics such as ampicillin, tetracycline and chloramphenicol may be added to the medium during the culturing.

When a microorganism transformed with a recombinant DNA prepared by using an inducible promoter is cultured, an inducer may be added to the medium, if necessary. For example, in the case of a microorganism transformed with a recombinant DNA in which lac promoter is used, isopropyl-β-D-thiogalactopyranoside or the like may be added to the medium, and in the case of a microorganism transformed with a recombinant-DNA in which trp promoter is used, indoleacrylic acid or the like may be added.

N-Acetylneuraminic acid can be produced by culturing a microorganism having the ability to produce N-acetylneuraminic acid, in which the activity to decompose N-acetylneuraminic acid is lost or reduced compared with a wild-type strain in a medium by the above-described culturing method, allowing N-acetylneuraminic acid to form and accumulate in the medium and recovering N-acetylneuraminic acid from the medium.

The following processes can be used for the production of N-acetylneuraminic acid:

(1) A process which comprises: allowing an enzyme source and a precursor of N-acetylneuraminic acid to be present in an aqueous medium, said enzyme source being a culture of a microorganism which has the ability to produce N-acetylneuraminic acid from a precursor of N-acetylneuraminic acid and in which the activity to decompose N-acetylneuraminic acid is lost or reduced compared with a wild-type strain or a treated matter of the culture; allowing N-acetylneuraminic acid to form and accumulate in the aqueous medium; and recovering N-acetylneuraminic acid from the aqueous medium.

(2) A process which comprises:
  allowing a culture of a microorganism which has the ability to produce a protein having N-acetylneuraminic acid synthase activity and the ability to produce phosphoenolpyruvic acid and in which the activity to decompose N-acetylneuraminic acid is lost or reduced compared with a wild-type strain or a treated matter of the culture as an enzyme source,
  N-acetylmannosamine, and
  a carbon source required by the microorganism for the production of phosphoenolpyruvic acid
  to be present in an aqueous medium;
  allowing N-acetylneuraminic acid to form and accumulate in the aqueous medium; and
  recovering N-acetylneuraminic acid from the aqueous medium.

(3) A process which comprises:
  allowing a culture of microorganism A which has the ability to produce a protein having N-acetylneuraminic acid synthase activity or a treated matter of the culture and a culture of microorganism B having the ability to produce phosphoenolpyruvic acid or a treated matter of the culture as enzyme sources, either one or both of said microorganisms A and B losing the activity to decompose N-acetylneuraminic acid or having the activity to decompose N-acetylneuraminic acid reduced compared with a wild-type strain,
  N-acetylmannosamine, and
  a carbon source required by the microorganism for the production of phosphoenolpyruvic acid
  to be present in an aqueous medium;
  allowing N-acetylneuraminic acid to form and accumulate in the aqueous medium; and
  recovering N-acetylneuraminic acid from the aqueous medium.

(4) A process which comprises:
  allowing a culture of a microorganism which has the ability to produce a protein having N-acetylneuraminic acid synthase activity, the ability to produce a protein having N-acetylglucosamine 2-epimerase activity and the ability to produce phosphoenolpyruvic acid and in which the activity to decompose N-acetylneuraminic acid is lost or reduced compared with a wild-type strain or a treated matter of the culture as an enzyme source,
  N-acetylglucosamine, and
  a carbon source required by the microorganism for the production of phosphoenolpyruvic acid
  to be present in an aqueous medium;
  allowing N-acetylneuraminic acid to form and accumulate in the aqueous medium; and
  recovering N-acetylneuraminic acid from the aqueous medium.

(5) A process which comprises:
  allowing a culture of microorganism C having one or two abilities selected from the group consisting of [1] the ability to produce a protein having N-acetylneuraminic acid synthase activity, [2] the ability to produce a protein having N-acetylglucosamine 2-epimerase activity and [3] the ability to produce phosphoenolpyruvic acid or a treated matter of the culture and a culture of microorganism D having all the abilities selected from [1]-[3] that are not possessed by the microorganism C or a treated matter of the culture as enzyme sources, either one or both of said microorganisms C and D losing the activity to decompose N-acetylneuraminic acid or having the activity to decompose N-acetylneuraminic acid reduced compared with a wild-type strain,
  N-acetylglucosamine, and
  a carbon source required by the microorganism having the ability to produce phosphoenolpyruvic acid for the production of phosphoenolpyruvic acid to be present in an aqueous medium;
allowing N-acetylneuraminic acid to form and accumulate in the aqueous medium; and
recovering N-acetylneuraminic acid from the aqueous medium.
(6) A process which comprises:
allowing a culture of microorganism E which has the ability to produce a protein having N-acetylneuraminic acid synthase activity or a treated matter of the culture, a culture of microorganism F which has the ability to produce a protein having N-acetylglucosamine 2-epimerase activity or a treated matter of the culture and a culture of microorganism G having the ability to produce phosphoenolpyruvic acid or a treated matter of the culture as enzyme sources, at least one of said microorganisms losing the activity to decompose N-acetylneuraminic acid or having the activity to decompose N-acetylneuraminic acid reduced compared with a wild-type strain,
N-acetylglucosamine, and
a carbon source required by the microorganism having the ability to produce phosphoenolpyruvic acid for the production of phosphoenolpyruvic acid
to be present in an aqueous medium;
allowing N-acetylneuraminic acid to form and accumulate in the aqueous medium; and
recovering N-acetylneuraminic acid from the aqueous medium.

The treated matters of a culture include concentrated culture, dried culture, cells obtained by centrifuging the culture, products obtained by treating the cells by various means such as drying, freeze-drying, treatment with a surfactant, ultrasonication, mechanical friction, treatment with a solvent, enzymatic treatment, protein fractionation and immobilization, an enzyme preparation obtained by extracting the cells, etc.

The amount of a culture or a treated matter of a culture used as an enzyme source in the production of N-acetylneuraminic acid is 0.1 mU/l-10,000 U/l as the activity of a culture of a single microorganism or a treated matter of the culture when a culture of a single microorganism or a treated matter of the culture is used as the enzyme source, or as the total activity of cultures of plural microorganisms or treated matters of the cultures when cultures of plural microorganisms or treated matters of the cultures are used as enzyme sources, one unit (U) being defined as the activity which can form 1 μmole of N-acetylneuraminic acid at 37° C. in one minute. Preferably, the amount of each microorganism used in the production of N-acetylneuraminic acid is 1-300 g/l as wet cells.

Precursors of N-acetylneuraminic acid such as N-acetylmannosamine and N-acetylglucosamine are used usually at a concentration of 1-300 g/l.

As the carbon sources required for the production of phosphoenolpyruvic acid, any carbon sources that are metabolized to phosphoenolpyruvic acid can be used. Preferably, carbohydrates such as glucose, fructose, sucrose, molasses containing them, starch and starch hydrolyzate are used and more preferably, glucose and fructose are used. These carbon sources may be added all together, in parts or continuously and are usually used at a concentration of 10-300 g/l.

Aqueous media used in the formation of N-acetylneuraminic acid include water, buffers such as phosphate buffer, carbonate buffer, acetate buffer, borate buffer, citrate buffer and Tris buffer, alcohols such as methanol and ethanol, esters such as ethyl acetate, ketones such as acetone, amides such as acetamide, etc. A culture broth of a microorganism used as the enzyme source can also be used as an aqueous medium.

If necessary, a surfactant or an organic solvent may be added for the formation of N-acetylneuraminic acid. Any surfactants that promote formation of N-acetylneuraminic acid may be used. Examples of the surfactants include nonionic surfactants such as polyoxyethylene octadecylamine (e.g., Nymeen S-215, NOF Corporation), cationic surfactants such as cetyltrimethylammonium bromide and alkyldimethyl benzylammonium chloride (e.g., Cation F2-40E, NOF Corporation), anionic surfactants such as lauroyl sarcosinate and tertiary amines such as alkyldimethylamine (e.g., Tertiary Amine FB, NOF Corporation), which may be used alone or in combination. The surfactant is usually used at a concentration of 0.1-50 g/l. As the organic solvent, xylene, toluene, aliphatic alcohols, acetone, ethyl acetate, etc. may be used usually at a concentration of 0.1-50 ml/l.

If necessary, magnesium chloride, manganese chloride, etc. can be added in the reaction process for the formation of N-acetylneuraminic acid.

The reaction for forming N-acetylneuraminic acid is carried out in an aqueous medium at pH5-10, preferably pH6-8, at 20-50° C., preferably at 30-40° C. for 1-96 hours.

N-Acetylneuraminic acid formed in the aqueous medium can be determined according to a known method [Anal. Biochem., 189, 151 (1990)].

N-Acetylneuraminic acid formed in the culture or the aqueous medium can be collected according to an ordinary method using ion exchange resins [Enzyme Microbiol. Technol., 20, 393 (1997)].

Figure 1:
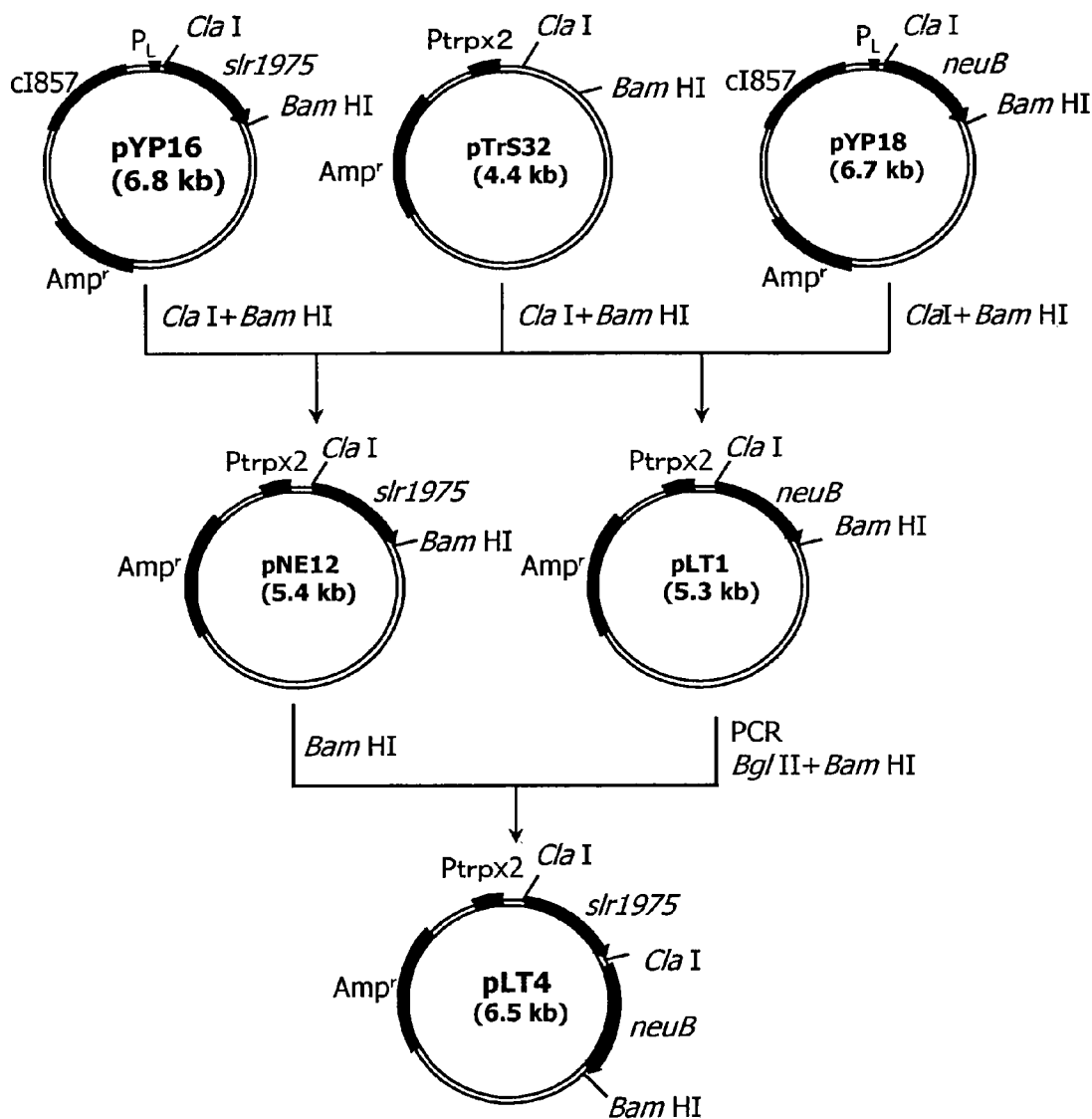
FIG. 1 shows the steps for constructing plasmid pLT4 expressing N-acetylneuraminic acid synthase gene and N-acetylglucosamine 2-epimerase gene.

Symbols in the drawing have the following meanings:
Ampr: Ampicillin resistance gene
$P_L$: $P_L$ promoter
Ptrpx2: Tryptophan tandem promoter
neuB: N-acetylneuraminic acid synthase gene
sln1975: N-Acetylglucosamine 2-epimerase gene

BEST MODES FOR CARRYING OUT THE INVENTION

EXAMPLE 1

Construction of a Strain Expressing N-Acetylneuraminic Acid Synthase and N-Acetylglucosamine 2-Epimerase After cleaving 0.2 μg of pYP18 (Japanese Published Unexamined Patent Application No. 136982/00) with restriction enzymes ClaI and BamHI, DNA fragments were separated by agarose gel electrophoresis, and a 1.1 kb DNA fragment comprising N-acetylneuraminic acid synthase gene derived from *Escherichia coli* was recovered using Gene Clean II Kit (Funakoshi). Then 0.1 μg of pTrS32 [prepared from *Escherichia coli* JM109/pTrS32 (FERM BP-5408)] was cleaved with restriction enzymes ClaI and BamHI, DNA fragments were separated by agarose gel electrophoresis, and a 4.2 kb DNA fragment was recovered in the same manner.

The 1.1 kb and 4.2 kb fragments were subjected to ligation using a ligation kit (Takara Shuzo) at 16° C. for 16 hours.

*Escherichia coli* NM522 was transformed using the ligation mixture according to the known method described above, and the transformant was spread on LB agar medium [10 g/l Bacto-tryptone (Difco Laboratories Inc.), 10 g/l yeast extract, 5 g/l sodium chloride, 0.15 g/l agar] containing 50 μg/ml ampicillin and cultured overnight at 30° C.

A plasmid was extracted from a colony of the transformant that grew on the above medium according to the known method described above to obtain pLT1, a plasmid for expression of N-acetylneuraminic acid synthase gene. The structure of the plasmid was confirmed by digestion with restriction enzymes (FIG. 1).

Next, 0.2 μg of pYP16 (Japanese Published Unexamined Patent Application No. 136982/00) was cleaved with restriction enzymes ClaI and BamHI, followed by separation of DNA fragments by agarose gel electrophoresis, and a 1.2 kb DNA fragment comprising N-acetylglucosamine 2-epimerase gene derived from a microorganism belonging to the genus *Synechocystis* was recovered using Gene Clean II Kit. Then, 0.1 μg of pTrS32 was cleaved with restriction enzymes ClaI and BamHI, followed by separation of DNA fragments by agarose gel electrophoresis, and a 4.2 kb DNA fragment was recovered in the same manner.

The 1.2 kb and 4.2 kb fragments were subjected to ligation using a ligation kit at 16° C. for 16 hours.

*Escherichia coli* NM522 was transformed using the ligation mixture according to the known method described above, and the transformant was spread on LB agar medium containing 50 μg/ml ampicillin and cultured overnight at 30° C. A plasmid was extracted from a colony of the transformant that grew on the above medium according to the known method described above to obtain pNE12, a plasmid for expression of N-acetylglucosamine 2-epimerase gene. The structure of the plasmid was confirmed by digestion with restriction enzymes (FIG. 1).

DNAs having the nucleotide sequence shown in SEQ ID NO: 1 and that shown in SEQ ID NO: 2, respectively, were synthesized by using Model 8905 DNA Synthesizer produced by PerSeptive Biosystems. PCR was carried out using the DNAs as a set of primers and pLT1 plasmid DNA as a template in the following manner. That is, PCR was carried out by 30 cycles, one cycle consisting of reaction at 94° C. for one minute, reaction at 37° C. for 2 minutes and reaction at 72° C. for 3 minutes, using 40 μl of a reaction mixture comprising 0.1 μg of pLT1 plasmid DNA, 0.5 μmol/l each of the above primer DNAs, 2.5 units of Pfu DNA polymerase (Stratagene), 4 μl of buffer for Pfu DNA polymerase (10×) (Stratagene) and 200 μmol/l each of deoxyNTPs to obtain a PCR product of about 1.1 kb.

One-tenth of the resulting reaction mixture was subjected to agarose gel electrophoresis to confirm that the desired fragment was amplified. Then, the remaining reaction mixture was mixed with an equal amount of phenol/chloroform saturated with TE, followed by centrifugation. The obtained upper layer was mixed with a two-fold volume of cold ethanol and allowed to stand at −80° C. for 30 minutes. The resulting solution was centrifuged to obtain a DNA precipitate.

The DNA precipitate was dissolved in 20 μl of TE [10 mmol/l Tris-HCl, 1 mmol/l EDTA (pH8.0)], and 5 μl of the solution was subjected to reaction to cleave the DNA with restriction enzymes BgIII and BamNI. DNA fragments were separated by agarose gel electrophoresis, and a 1.1 kb DNA fragment comprising N-acetylneuraminic acid synthase gene was recovered using Gene Clean II Kit.

After cleaving 0.2 μg of pNE12 with a restriction enzyme BamHI, DNA fragments were separated by agarose gel electrophoresis, and a 5.4 kb DNA fragment was recovered in the same manner.

The 1.1 kb and 5.4 kb fragments were subjected to ligation using a ligation kit at 16° C. for 16 hours.

*Escherichia coli* NM522 was transformed using the ligation mixture according to the known method described above, and the transformant was spread on LB agar medium containing 50 μg/ml ampicillin and cultured overnight at 30° C.

A plasmid was extracted from a colony of the transformant that grew on the above medium to obtain pLT4, a plasmid expressing N-acetylneuraminic acid synthase and N-acetylglucosamine 2-epimerase. The structure of the plasmid was confirmed by digestion with restriction enzymes (FIG. 1).

EXAMPLE 2

Acquisition of a Strain with Activity to Decompose N-Acetylneuraminic Acid Reduced

*Escherichia coli* HN0074 (FERM BP-4425) was inoculated into 30 ml of LB medium [10 g/l Bacto-trpton (Difco Laboratories Inc.), 10 g/l yeast extract, 5 g/l sodium chloride] in a 300-ml Erlenmeyer flask and cultured at 28° C. for 5 hours with shaking. The resulting culture was centrifuged at 3,000 r.p.m. at 4° C. for 10 minutes to recover the cells at the logarithmic growth phase. The cells were suspended in TM buffer [6.1 g/l Tris(hydroxymethyl)aminomethane, 5.8 g/l maleic acid, 0.1 g/l magnesium sulfate heptahydrate, 1 g/l ammonium sulfate, 0.5 g/l sodium citrate, pH6.0] containing 0.1 mg/ml N-methyl-N'-nitro-N-nitrosoguanidine, and mutagenesis was carried out at 37° C. for 30 minutes. The cells subjected to mutagenesis were collected by centrifugation, washed and then suspended in sterilized water. The suspension was spread on M9 minimal medium [3 g/l glucose, 6 g/l disodium hydrogenphosphate, 3 g/l potassium dihydrogenphosphate, 5 g/l sodium chloride, 1 g/l ammonium chloride, 0.24 g/l magnesium sulfate heptahydrate, 4 mg/l vitamin B1] containing 1.5% agar and on a plate medium comprising a medium same as the above M9 minimal medium containing agar except containing 0.75 g/l N-acetylneuraminic acid in place of glucose, respectively, and cultured at 37° C. for 2 days. A strain that grew favorably on the medium containing glucose but showed retarded growth or could not grow on the medium containing N-acetylneuraminic acid was selected to obtain *Escherichia coli* NAN8-71.

*Escherichia coli* HN0074 and NAN8-71 were inoculated into 30 ml of M9 minimal medium in 300-ml Erlenmeyer flasks, respectively, and cultured at 37° C. for 7 hours with stirring. Each of the cultures was centrifuged at 10,000 r.p.m. at 4° C. for 10 minutes to recover the cells.

Reaction was carried out using 0.1 ml of a reaction mixture comprising 120 g/l *Escherichia coli* HN0074 wet cells or NAN8-71 wet cells, 20 g/l N-acetylneuraminic acid, 4 g/l Nymeen S-215 and 10 ml/l xylene at 32° C. for 2 hours with shaking. As a result of analyzing the reaction products by HPLC, it was revealed that the residual ratio of N-acetylneuraminic acid was 85% for the parent strain HN0074 versus 98% for NAN8-71.

EXAMPLE 3

Production of N-Acetylneuraminic Acid

*Escherichia coli* NAN8-71 was transformed using plasmid pLT4 obtained in Example 1, and the transformant obtained was spread on LB agar medium containing 50 µg/ml ampicillin and cultured overnight at 30° C. to obtain *Escherichia coli* NAN8-71/pLT4.

*Escherichia coli* NAN8-71/pLT4 was inoculated into 150 ml of LB medium containing 50 µg/ml ampicillin in a 1-1 Erlenmeyer flask with baffles and cultured at 30° C. with shaking at 220 rpm for 17 hours. Then, 150 ml of the culture was inoculated into 3 l of M9 medium [5 g/l glucose, 6 g/l disodium hydrogenphosphate, 3 g/l potassium dihydrogenphosphate, 5 g/l sodium chloride, 1 g/l ammonium chloride, 2.4 g/l magnesium sulfate heptahydrate, 10 mg/l manganese sulfate monohydrate, 200 mg/l ferrous sulfate heptahydrate, 8 mg/l vitamin B1, 5 g/l peptone (Kyokuto Pharmaceutical)] containing 50 µg/ml ampicillin in a 5-1 jar fermentor and cultured at 30° C. for 6.5 hours under the conditions of stirring at 600 rpm and aeration at 3 l/min. During the culturing, the pH of the culture was maintained at 7.0 with 28% aqueous ammonia. After the completion of culturing, the culture was centrifuged to obtain wet cells. The wet cells could be stored at −20° and could be used after thawing as needed.

A reaction mixture (30 ml) comprising 200 g/l *Escherichia coli* NAN8-71/pLT4 wet cells, 90 g/l N-acetylglucosamine, 50 g/l glucose, 4 g/l Nymeen S-215 and 10 ml/l xylene was put into a 200-ml beaker and subjected to reaction at 32° C. for 24 hours with stirring (900 rpm) using a magnetic stirrer. During the reaction, the pH of the reaction mixture was maintained at 7.2 with 2 mol/l sodium hydroxide solution, and if necessary, glucose was added thereto.

After the completion of reaction, the reaction product was analyzed by HPLC, and it was confirmed that 35 g/l N-acetylneuraminic acid was formed and accumulated in the reaction mixture. When a similar reaction was carried out using *Escherichia coli* HN0074/pLT4 wet cells, the amount of accumulation of N-acetylneuraminic acid was 12 g/l.

INDUSTRIAL APPLICABILITY

According to the present invention, N-acetylneuraminic acid can be produced efficiently.

[Sequence Listing Free Text]

SEQ ID NO: 1—Description of the artificial sequence: synthetic DNA

SEQ ID NO: 2—Description of the artificial sequence: synthetic DNA

---

The invention claimed is:

1. A process for producing N-acetylneuraminic acid which comprises:
allowing
a culture of a microorganism which has the ability to produce a protein having N-acetylneuraminic acid synthase activity, the ability to produce a protein having N-acetylglucosamine 2-epimerase activity and the ability to produce phosphoenolpyruvic acid and in which sialic acid aldolase activity is lost or reduced compared with a wild-type strain or a treated matter of the culture as an enzyme source,
N-acetylglucosamine, and
a carbon source required by the microorganism for the production of phosphoenolpyruvic acid
to be present in an aqueous medium;
allowing N-acetylneuraminic acid to form and accumulate in the aqueous medium; and
recovering N-acetylneuraminic acid from the aqueous medium.

2. The process according to claim 1 wherein the carbon source required for the production of phosphoenolpyruvic acid is glucose or fructose.

3. The process according to claim 1 or 2, wherein the microorganism is selected from the group consisting of microorganisms belonging to the genera *Escherichia*, *Corynebacterium* and *Bacillus*.

4. The process according to claim 3, wherein the microorganism belonging to the genus *Escherichia* is *Escherichia coli* NAN8-71 (FERM BP-7908) in which the activity to decompose N-acetylneuraminic acid is reduced compared with a wild-type strain.

* * * * *

UNITED STATES PATENT AND TRADEMARK OFFICE
CERTIFICATE OF CORRECTION

PATENT NO. : 7,329,514 B2
APPLICATION NO. : 10/504511
DATED : February 12, 2008
INVENTOR(S) : Mari Shiba et al.

It is certified that error appears in the above-identified patent and that said Letters Patent is hereby corrected as shown below:

COLUMN 3:

Line 6, "of[1]" should read --of [1]--.

COLUMN 5:

Line 65, "X phage" should read --λ phage--.

COLUMN 6:

Line 4, "8" should be deleted.

COLUMN 12:

Line 15, "N-acetylneuraminate synthasse" should read --N-acetylneuraminic acid synthase--.

COLUMN 16:

Line 37, "ammoniagenes" should read --*ammoniagenes*--; and
Line 47, "synthase" should be deleted.

COLUMN 17:

Line 1, "techniques. The" should read --techniques. ¶ The--;
Line 2, "N" should be deleted;
Line 3, "acetylneuraminate synthase" should be deleted; and
Line 5, "phosphoenoipyruvic" should read --phosphoenolpyruvic--.

COLUMN 19:

Line 39, "recombinant-DNA" should read --recombinant DNA--; and
Line 41, "N-Acetylneuraminic" should read --N-acetylneuraminic--.

COLUMN 20:

Line 50, "of[1]" should read --of [1]--.

UNITED STATES PATENT AND TRADEMARK OFFICE
CERTIFICATE OF CORRECTION

PATENT NO. : 7,329,514 B2
APPLICATION NO. : 10/504511
DATED : February 12, 2008
INVENTOR(S) : Mari Shiba et al.

It is certified that error appears in the above-identified patent and that said Letters Patent is hereby corrected as shown below:

COLUMN 22:

Line 26, "N-Acetylneuraminic" should read --N-acetylneuraminic--;
Line 29, "N-Acetylneuraminic" should read --N-acetylneuraminic--; and
Line 39, "Ampr:" should read --$Amp^r$:--.

COLUMN 23:

Line 64, "BgIII and BamNI." should read --Bg1II and BamHI.--.

COLUMN 30:

Line 51, "claim 1" should read --claim 1,--.

Signed and Sealed this

Fourteenth Day of October, 2008

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 1
ccgcaagatc tcgtaaaaag ggtatcgat                                    29

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 2
tttggatcct cattattccc cctgattttt gaa                               33

<210> SEQ ID NO 3
<211> LENGTH: 297
<212> TYPE: PRT
<213> ORGANISM: Escherichia coli

<400> SEQUENCE: 3

Met Ala Thr Asn Leu Arg Gly Val Met Ala Ala Leu Leu Thr Pro Phe
  1               5                  10                  15

Asp Gln Gln Gln Ala Leu Asp Lys Ala Ser Leu Arg Arg Leu Val Gln
             20                  25                  30

Phe Asn Ile Gln Gln Gly Ile Asp Gly Leu Tyr Val Gly Gly Ser Thr
```

```
                35                  40                  45
Gly Glu Ala Phe Val Gln Ser Leu Ser Glu Arg Glu Gln Val Leu Glu
 50                  55                  60

Ile Val Ala Glu Glu Ala Lys Gly Lys Ile Lys Leu Ile Ala His Val
 65                  70                  75                  80

Gly Cys Val Ser Thr Ala Glu Ser Gln Gln Leu Ala Ala Ser Ala Lys
                 85                  90                  95

Arg Tyr Gly Phe Asp Ala Val Ser Ala Val Thr Pro Phe Tyr Tyr Pro
                100                 105                 110

Phe Ser Phe Glu Glu His Cys Asp His Tyr Arg Ala Ile Ile Asp Ser
            115                 120                 125

Ala Asp Gly Leu Pro Met Val Val Tyr Asn Ile Pro Ala Leu Ser Gly
130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
290                 295

<210> SEQ ID NO 4
<211> LENGTH: 891
<212> TYPE: DNA
<213> ORGANISM: Escherichia coli

<400> SEQUENCE: 4 atg gca acg aat tta cgt ggc gta atg gct gca ctc ctg act cct ttt      48
Met Ala Thr Asn Leu Arg Gly Val Met Ala Ala Leu Leu Thr Pro Phe
 1               5                  10                  15 gac caa caa caa gca ctg gat aaa gcg agt ctg cgt cgc ctg gtt cag      96
Asp Gln Gln Gln Ala Leu Asp Lys Ala Ser Leu Arg Arg Leu Val Gln
                 20                  25                  30 ttc aat att cag cag ggc atc gac ggt tta tac gtg ggt ggt tcg acc     144
Phe Asn Ile Gln Gln Gly Ile Asp Gly Leu Tyr Val Gly Gly Ser Thr
             35                  40                  45 ggc gag gcc ttt gta caa agc ctt tcc gag cgt gaa cag gta ctg gaa     192
Gly Glu Ala Phe Val Gln Ser Leu Ser Glu Arg Glu Gln Val Leu Glu
 50                  55                  60 atc gtc gcc gaa gag gcg aaa ggt aag att aaa ctc atc gcc cac gtc     240
Ile Val Ala Glu Glu Ala Lys Gly Lys Ile Lys Leu Ile Ala His Val
 65                  70                  75                  80 ggt tgc gtc agc acc gcc gaa agc caa caa ctt gcg gca tcg gct aaa     288
```

-continued

```
                Gly Cys Val Ser Thr Ala Glu Ser Gln Gln Leu Ala Ala Ser Ala Lys
                                85                  90                  95 cgt tat ggc ttc gat gcc gtc tcc gcc gtc acg ccg ttc tac tat cct          336
Arg Tyr Gly Phe Asp Ala Val Ser Ala Val Thr Pro Phe Tyr Tyr Pro
                100                 105                 110 ttc agc ttt gaa gaa cac tgc gat cac tat cgg gca att att gat tcg          384
Phe Ser Phe Glu Glu His Cys Asp His Tyr Arg Ala Ile Ile Asp Ser
            115                 120                 125 gcg gat ggt ttg ccg atg gtg gtg tac aac att cca gcc ctg agt ggg          432
Ala Asp Gly Leu Pro Met Val Val Tyr Asn Ile Pro Ala Leu Ser Gly
    130                 135                 140 gta aaa ctg acc ctg gat cag atc aac aca ctt gtt aca ttg cct ggc          480
Val Lys Leu Thr Leu Asp Gln Ile Asn Thr Leu Val Thr Leu Pro Gly
145                 150                 155                 160 gta ggt gcg ctg aaa cag acc tct ggc gat ctc tat cag atg gag cag          528
Val Gly Ala Leu Lys Gln Thr Ser Gly Asp Leu Tyr Gln Met Glu Gln
                165                 170                 175 atc cgt cgt gaa cat cct gat ctt gtg ctc tat aac ggt tac gac gaa          576
Ile Arg Arg Glu His Pro Asp Leu Val Leu Tyr Asn Gly Tyr Asp Glu
                180                 185                 190 atc ttc gcc tct ggt ctg ctg gcg ggc gct gat ggt ggt atc ggc agt          624
Ile Phe Ala Ser Gly Leu Leu Ala Gly Ala Asp Gly Gly Ile Gly Ser
            195                 200                 205 acc tac aac atc atg ggc tgg cgc tat cag ggg atc gtt aag gcg ctg          672
Thr Tyr Asn Ile Met Gly Trp Arg Tyr Gln Gly Ile Val Lys Ala Leu
    210                 215                 220 aaa gaa ggc gat atc cag acc gcg cag aaa ctg caa act gaa tgc aat          720
Lys Glu Gly Asp Ile Gln Thr Ala Gln Lys Leu Gln Thr Glu Cys Asn
225                 230                 235                 240 aaa gtc att gat tta ctg atc aaa acg ggc gta ttc cgc ggc ctg aaa          768
Lys Val Ile Asp Leu Leu Ile Lys Thr Gly Val Phe Arg Gly Leu Lys
                245                 250                 255 act gtc ctc cat tat atg gat gtc gtt tct gtg ccg ctg tgc cgc aaa          816
Thr Val Leu His Tyr Met Asp Val Val Ser Val Pro Leu Cys Arg Lys
                260                 265                 270 ccg ttt gga ccg gta gat gaa aaa tat ctg cca gaa ctg aag gcg ctg          864
Pro Phe Gly Pro Val Asp Glu Lys Tyr Leu Pro Glu Leu Lys Ala Leu
            275                 280                 285 gcc cag cag ttg atg caa gag cgc ggg                                      891
Ala Gln Gln Leu Met Gln Glu Arg Gly
    290                 295
```